(12) United States Patent
Bremer et al.

(10) Patent No.: US 12,070,333 B2
(45) Date of Patent: Aug. 27, 2024

(54) WEARABLE DEVICE FOR SENSING VITAL SIGNS

(71) Applicant: Welch Allyn, Inc., Skaneateles Falls, NY (US)

(72) Inventors: Edward Bremer, Victor, NY (US); Brian L. Jovanovski, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 608 days.

(21) Appl. No.: 17/329,277

(22) Filed: May 25, 2021

(65) Prior Publication Data

US 2021/0369203 A1 Dec. 2, 2021

Related U.S. Application Data

(60) Provisional application No. 63/031,804, filed on May 29, 2020.

(51) Int. Cl.
*A61B 5/00* (2006.01)
*A61B 5/0205* (2006.01)
(Continued)

(52) U.S. Cl.
CPC .......... *A61B 5/6823* (2013.01); *A61B 5/0205* (2013.01); *A61B 5/14552* (2013.01);
(Continued)

(58) Field of Classification Search
CPC .............. A61B 5/1455; A61B 5/14551; A61B 5/14552; A61B 5/6823; A61B 5/0205;
(Continued)

(56) References Cited

U.S. PATENT DOCUMENTS 4,380,014 A * 4/1983 Howard ............. H01Q 13/0266
343/786
7,894,869 B2 * 2/2011 Hoarau ................ A61B 5/6838
600/323
(Continued)

FOREIGN PATENT DOCUMENTS

CA 3045025 A1 6/2018
EP 3457926 A1 3/2019
(Continued)

OTHER PUBLICATIONS

European Search Report, Application No. EP 21 176 738, dated Oct. 19, 2021, 8 pages.
(Continued)

*Primary Examiner* — Eric F Winakur
(74) *Attorney, Agent, or Firm* — Merchant & Gould P.C.

(57) ABSTRACT

A wearable device for sensing vital signs includes a flexible housing, at least one light emitter attached to the flexible housing, the at least one light emitter configured to emit optical signals, and light sensors attached to the flexible housing. The light sensors are positioned on opposite sides of the at least one light emitter. The flexible housing is structured to attach to a skin surface and flex at least partially around an anatomical structure enabling the light sensors to receive both reflective and transmissive optical signals near a chest of a subject.

18 Claims, 11 Drawing Sheets

(51) Int. Cl.
*A61B 5/021* (2006.01)
*A61B 5/024* (2006.01)
*A61B 5/1455* (2006.01)

(52) U.S. Cl.
CPC ............ *A61B 5/6832* (2013.01); *A61B 5/021* (2013.01); *A61B 5/02433* (2013.01); *A61B 2562/0238* (2013.01)

(58) Field of Classification Search
CPC ... A61B 5/6832; A61B 5/021; A61B 5/02433; A61B 5/0238
See application file for complete search history.

(56) References Cited

U.S. PATENT DOCUMENTS

| | | | |
|---|---|---|---|
| 11,517,225 B2 * | 12/2022 | Bomsta | ............ A61B 5/14542 |
| 2013/0035562 A1 | 2/2013 | Besko | |
| 2013/0261415 A1 | 10/2013 | Ashe et al. | |
| 2016/0240721 A1 | 8/2016 | Chu et al. | |
| 2016/0361004 A1 | 12/2016 | Lange et al. | |
| 2017/0127959 A1 | 5/2017 | Paulussen et al. | |
| 2017/0156651 A1 | 6/2017 | Arias et al. | |
| 2019/0142625 A1 * | 5/2019 | Goff | ................ A61B 5/4818 600/538 |
| 2019/0167211 A1 | 6/2019 | Everman et al. | |
| 2019/0261859 A1 | 8/2019 | Dietiker | |
| 2019/0387972 A1 | 12/2019 | Hu et al. | |
| 2020/0029850 A1 | 1/2020 | Tang et al. | |
| 2020/0060555 A1 | 2/2020 | Lamego et al. | |
| 2020/0121258 A1 | 4/2020 | Zhu et al. | |
| 2020/0214579 A1 * | 7/2020 | Phillips | ............. A61B 5/02141 |

FOREIGN PATENT DOCUMENTS

| | | |
|---|---|---|
| EP | 3626159 A1 | 3/2020 |
| WO | 2016022295 A1 | 2/2016 |
| WO | 2017201419 A1 | 11/2017 |
| WO | 2017202120 A1 | 11/2017 |
| WO | 2019213054 A1 | 11/2019 |
| WO | 2019226692 A1 | 11/2019 |
| WO | 2020023681 A1 | 1/2020 |

OTHER PUBLICATIONS

"M-LNCS Series, LNCS Series Adult, Pediatric, Infant, Neonatal and Preterm Sp02 adhesive sensors." eIFU Indicator. Masimo Corporation, 5 pages, 2019.

"Monitoring Solutions for Patients with Low Perfusion." Masimo Corporation, 2 pages, 2019.

Examination report No. 1 for standard patent application, Australian Patent Application No. 2021203447, Nov. 26, 2021, 11 pages.

* cited by examiner

WEARABLE DEVICE FOR SENSING VITAL SIGNS

BACKGROUND

A pulse oximeter is one type of device that is often used to measure peripheral oxygen saturation ($SpO_2$). A pulse oximeter typically operates by illuminating a skin surface with light and measuring changes in light absorption in the blood under the skin.

In transmission-mode pulse oximetry, a pulse oximeter has light emitters and light sensors positioned on opposite sides of an anatomical structure such that the light from the light emitters passes through the anatomical structure and is received by the light sensors on the other side. A possible disadvantage of transmission-mode pulse oximetry is that it is limited to sensing locations where it is possible to pass light through such as a finger, toe, or earlobe.

On the other hand, reflection-mode pulse oximetry uses light emitters and light sensors on the same side of an anatomical area, which allows for diverse sensing locations such as the forehead, forearm, abdomen, and leg. However, reflection-mode pulse oximetry may provide poor signal quality, which can lead to unreliable and inaccurate $SpO_2$ measurements.

SUMMARY

In general terms, the present disclosure relates to a wearable device for sensing vital signs. In one possible configuration, the wearable device provides a technical effect by sensing blood oxygen saturation level when attached to a portion of a subject's body that is ordinarily unable to provide useful data for measuring blood oxygen saturation. Various aspects are described in this disclosure, which include, but are not limited to, the following aspects.

In one aspect, a wearable device for sensing vital signs comprises a flexible housing; at least one light emitter attached to the flexible housing, the at least one light emitter configured to emit optical signals; and light sensors attached to the flexible housing, the light sensors being positioned to at least partially oppose the at least one light emitter. The flexible housing attaches to a skin surface and flexes at least partially around an anatomical structure enabling the light sensors to receive both reflective and transmissive optical signals near a chest of a subject.

In another aspect, a method of measuring peripheral oxygen saturation comprises attaching a wearable device around an anatomical structure near a chest such that the wearable device partially surrounds the anatomical structure near the chest; using the wearable device to obtain optical signals near the chest; and using the obtained optical signals to calculate peripheral oxygen saturation.

In another aspect, a method of measuring cuff-less blood pressure comprises: attaching a wearable device around an anatomical structure near a chest such that the wearable device partially surrounds the anatomical structure near the chest; using the wearable device to obtain optical signals near the chest; using the obtained optical signals to calculate a photoplethysmogram; and using the photoplethysmogram to calculate cuff-less blood pressure.

In another aspect, a wearable device for sensing vital signs comprises a flexible housing; an optical unit positioned inside the flexible housing, the optical unit including: light emitters that emit a transmission sequence of optical signals; light sensors positioned on opposite sides of the light emitters; and wherein the flexible housing is structured to attach to a skin surface and flex around an anatomical structure enabling the light sensors to receive both reflective and transmissive optical signals near a chest of a subject.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
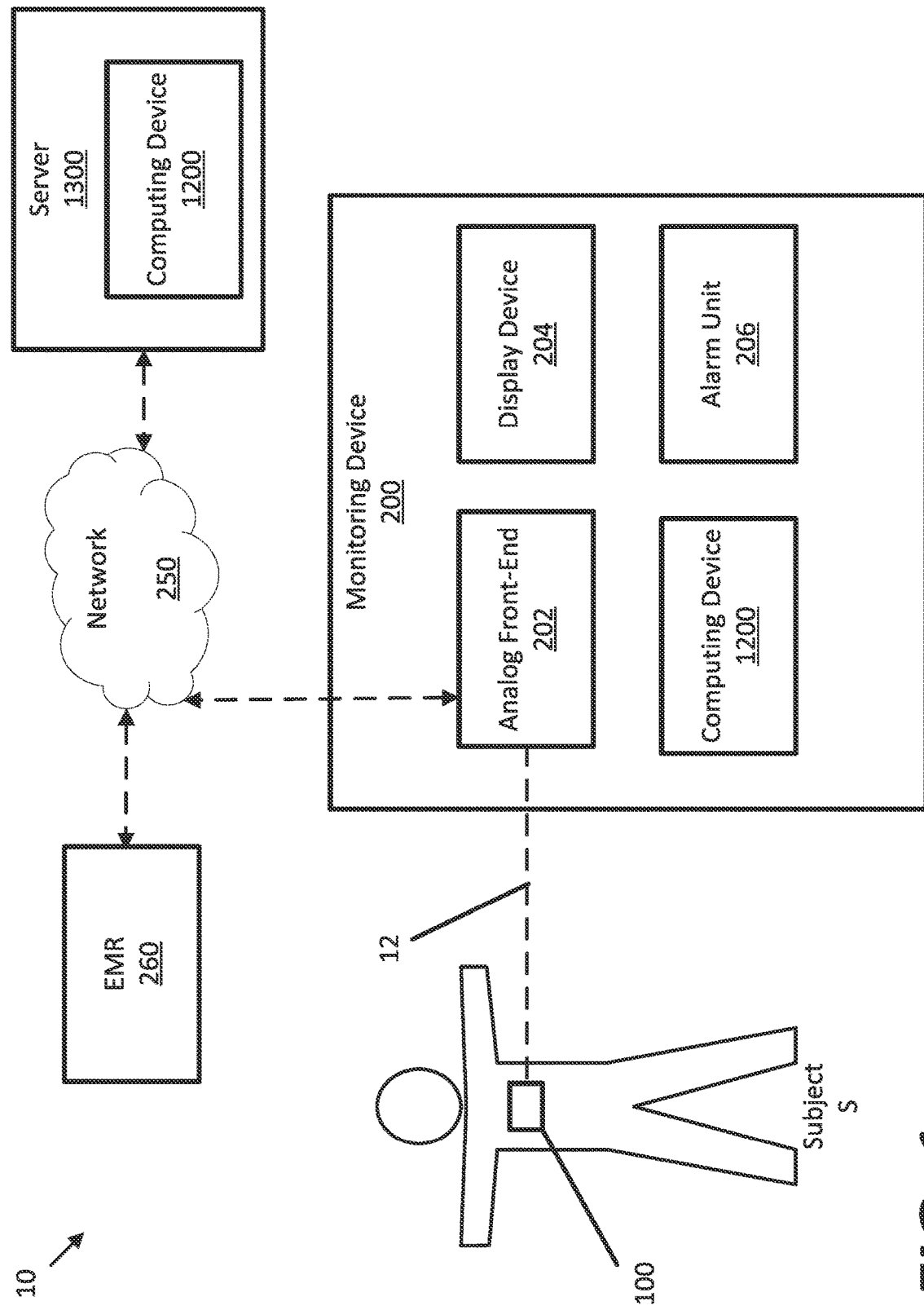
FIG. 1 schematically illustrates a patient monitoring system.

FIG. 1 schematically illustrates a patient monitoring system 10 that includes a wearable device 100 worn by a subject S to measure one or more vital signs. The wearable device 100 may be flexible such that it can at least partially surround a skin surface near the chest of the subject S such that the wearable device 100 may receive both reflective and transmissive optical signals. By receiving, for example, both reflective and transmissive optical signals, the wearable device 100 can reduce noise and improve signal quality to provide more reliable and accurate $SpO_2$ and PPG measurements when the wearable device 100 is worn near the chest of the subject S.

The wearable device 100 is "wearable" in that it can be applied to a skin surface and will resist unintentional dislodgement over a specified interval of time. For example, the wearable device 100 can be worn continuously by the subject S for five or more days.

The wearable device 100 detects optical signals for measuring a vital sign. In some embodiments, the optical signals are used to measure peripheral oxygen saturation ($SpO_2$) of the subject S. In such embodiments, the optical signals include differences in light absorption between oxygenated and deoxygenated hemoglobin in the blood of the subject S.

In some embodiments, the optical signals are used to measure a photoplethysmogram (PPG) of the subject S by detecting changes in light absorption in a microvascular bed of tissue of the subject S. In some embodiments, the PPG measured from the optical signals is used to measure a cuff-less blood pressure of the subject S.

The wearable device 100 can be attached to any area of the body of the subject S to detect the optical signals. In certain embodiments, the wearable device 100 is attached on or near the chest of the subject S to detect the optical signals. Advantageously, the wearable device 100 is flexible such that it is can partially surround the clavicle (i.e., collarbone), shoulder blade, a fold of skin in the axilla (i.e., armpit), or another area near the chest of the subject S.

As shown in FIG. 1, the wearable device 100 transmits electrical signals 12 that are acquired from light sensors on the wearable device 100 to a monitoring device 200. In certain embodiments, the monitoring device 200 is a smartphone, tablet computer, or other portable computing device. In further embodiments, the monitoring device 200 is a vital signs monitor that is fixed to a wall or to another device within a healthcare facility such as a bed, or a portable spot monitor that can be moved about the facility.

The electrical signals 12 are transmitted through a connection to an analog front-end 202 of the monitoring device 200. In some examples, the analog front-end 202 of the monitoring device 200 can drive an optical unit 110 of the wearable device 100 that includes light emitters 112 and light sensors 114 (see FIG. 2).

In some embodiments, the connection to the analog front-end 202 is wireless such that the wearable device 100 is not tethered to the monitoring device 200. Advantageously, a wireless connection allows the subject S to move freely relative to the monitoring device 200 to improve the mobility of the subject S while wearing the wearable device. Examples of wireless connections between the wearable device 100 and monitoring device 200 include, without limitation, Bluetooth, Wi-Fi, RFID, Near-Field Communication (NFC), ZigBee, and the like.

In some embodiments, the electrical signals 12 include raw data that is processed by the monitoring device 200. The monitoring device 200 includes a computing device 1200 for processing the electrical signals 12 into a measured vital sign such as $SpO_2$ or PPG. The computing device 1200 includes at least one processing unit and a memory described in more detail below with reference to FIG. 12. The memory of the computing device 1200 stores one or more algorithms that when executed by the processing unit perform one or more of the methods, operations, computations, or processes described herein.

The patient monitoring system 10 can include a server 1300 that is remotely located with respect to the wearable device 100 and monitoring device 200. In certain embodiments, the monitoring device 200 transmits the electrical signals 12 as raw data to the server 1300 via a network 250, and the server 1300 uses a computing device 1200 to process the electrical signals 12 into a measured vital sign. The measured vital sign can then be communicated back to the monitoring device 200 and/or wearable device 100 via the network 250.

The network 250 can include any type of wired or wireless connections or any combinations thereof. Examples of wireless connections include digital cellular network connections such as 5G. In some embodiments, wireless connections can be accomplished using, without limitation, Bluetooth, Wi-Fi, RFID, NFC, ZigBee, and the like.

In certain embodiments, the wearable device 100 processes the electrical signals 12 into a measured vital sign. For example, the wearable device 100 can include a computing device having at least one processing unit and a memory (see, for example, FIG. 2).

In further embodiments, the processing of the detected optical signals into a measured vital sign is shared between the wearable device 100, monitoring device 200, and/or server 1300, and may vary depending on one or more parameters including, without limitation, the processing capacities of the respective devices, battery levels of the respective devices, energy cost of transmitting the electrical signals 12, level of noise in the optical signals, and/or the link rate and link reliability for linking the respective devices together, and the like.

In certain embodiments, the monitoring device 200 includes a display device 204 to display a measured vital sign such as $SpO_2$, PPG, and cuff-less blood pressure of the subject S. The $SpO_2$, PPG, and cuff-less blood pressure measurements are displayable on the display device 204 numerically, graphically, or in any combination of numerical and graphical representations.

In certain embodiments, the monitoring device 200 includes an alarm unit 206. The alarm unit 206 generates one or more alarms when the $SpO_2$, PPG, and cuff-less blood pressure measurements are outside a predetermined range of values. The alarm unit 206 generates audible alarms and/or visual alarms on the display device 204. In addition to or as an alternative to generating audible and/or visual alarms, the alarm unit 206 generates a message sent directly to one or more caregivers to notify the caregivers that the $SpO_2$, PPG, and cuff-less blood pressure measurements exceed the predetermined range of values. Examples of such messages can include text messages, instant messages, emails, and the like.

In certain embodiments, the monitoring device 200 uses the network 250 to automatically transfer the $SpO_2$, PPG, and cuff-less blood pressure measurements to an electronic medical record system 260 (alternatively termed electronic health record, EMR/EHR). Advantageously, the $SpO_2$, PPG, and cuff-less blood pressure measurements are automatically stored in an electronic medical record or electronic health record of the subject S in real-time.

Figure 2:
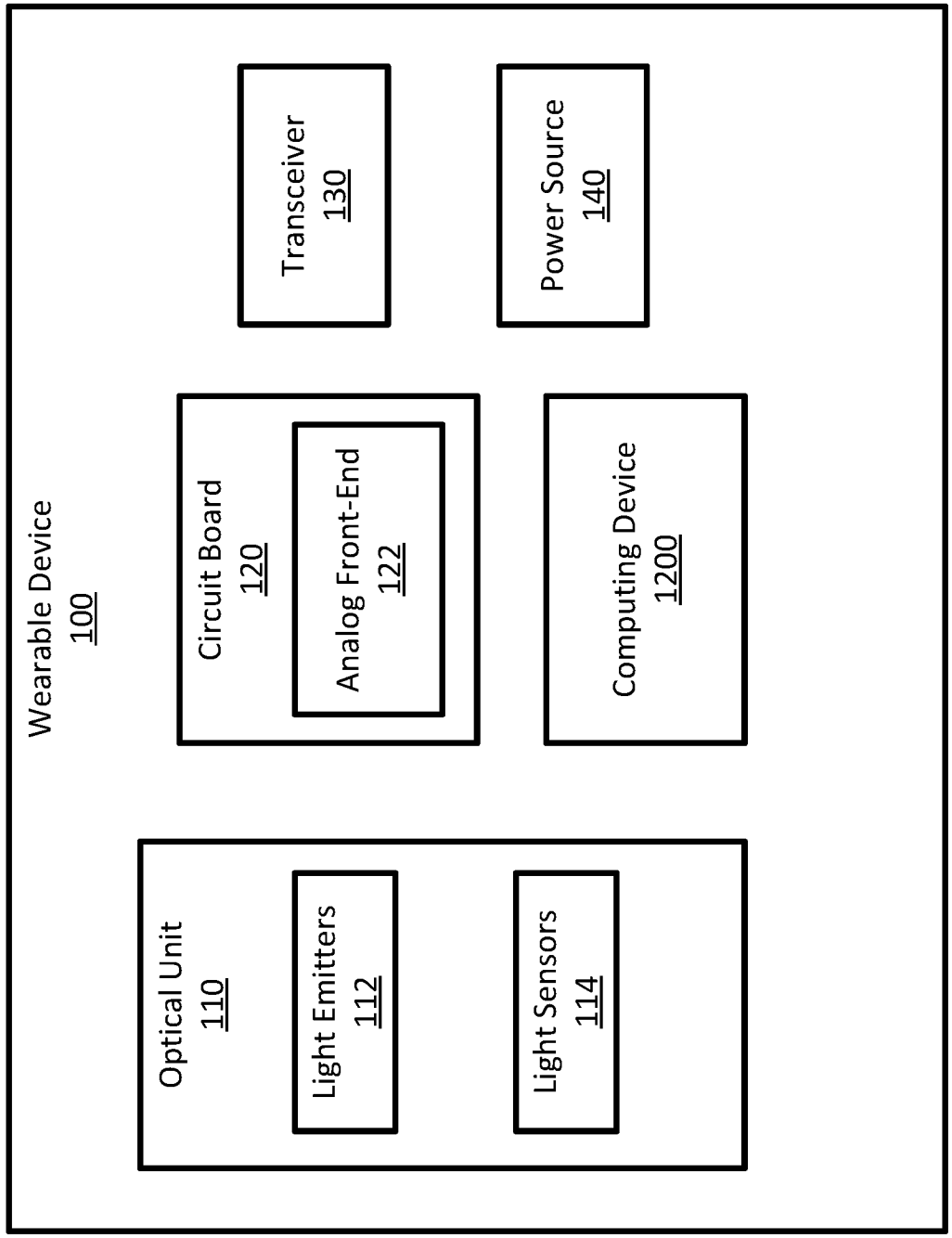
FIG. 2 schematically illustrates a wearable device for sensing vital signs.

FIG. 2 schematically illustrates the wearable device 100. As shown in FIG. 2, the wearable device 100 includes an optical unit 110 that detects the optical signals. As will be described in more detail, the optical signals can advantageously include both transmissive and reflective optical signals. In certain embodiments, the optical unit 110 is a photoplethysmogram (PPG) sensor. Preferably, the optical unit 110 can be combined with other sensors in a single assembly to provide a small, lightweight, and easy to integrate sensor package.

The optical unit 110 includes one or more light emitters 112 that emit optical signals to illuminate blood vessels under a skin surface of the subject S. The light emitters 112 may emit in a transmission sequence optical signals in the form of infrared (IR) and visible red light. For example, the light emitters 112 can alternate between emitting infrared and visible red light. The light emitters 112 can include light-emitting diodes (LEDs), lasers, lamps, and the like. The light emitters 112 can also be multi-wavelength light emitters that emit ultra violet, violet blue, yellow, green, and additional color spectrums for collecting multi-spectral measurements of the tissue and fluid (e.g., blood) under a skin surface of the subject S.

In some embodiments, the optical signals emitted from the light emitters 112 are programmed to be pulsed at predetermined intervals of time such that the light emitters 112 do not constantly emit the optical signals while the wearable device 100 is worn. Advantageously, this can reduce electrical power consumption by the wearable device 100, especially when the wearable device 100 is worn by the subject S for an extended period of time.

The optical unit 110 includes one or more light sensors 114 to receive optical signals reflected back from the blood vessels (reflection-mode pulse oximetry) and optical signals transmitted through the blood vessels (transmission-mode pulse oximetry). The light sensors 114 respond to the transmission sequence of infrared and visible red light from the light emitters 112 to detect changes in the infrared and red-light absorption in the blood where the wearable device 100 is attached. In some examples, the light sensors 114 are photodetectors or photodiodes.

Absorption of infrared and visible red light differs significantly between blood loaded with oxygen and blood lacking oxygen. For example, oxygenated hemoglobin absorbs more infrared light and allows more visible red light to pass through. Deoxygenated hemoglobin allows more infrared light to pass through and absorbs more visible red light The amount of absorption for each wavelength of light emitted from the light emitters 112 is measured by the light sensors 114. The ratio of the visible red light absorption to the infrared light absorption is calculated to determine a ratio of oxygenated hemoglobin to deoxygenated hemoglobin, and the ratio is converted into an $SpO_2$ measurement.

The amount of absorption for each wavelength of light can also be used to generate a photoplethysmogram (PPG) and to evaluate blood perfusion. As described above, the PPG can be used to measure a cuff-less blood pressure of the subject S.

In some examples, the wearable device 100 includes only the optical unit 110 (e.g., including the light emitters 112, light sensors 114), and a connection to the analog front end 202 of the monitoring device 200. In alternative examples, such as the one shown in FIG. 2, the wearable device 100 can operate in a stand-alone mode to measure PPG and $SpO_2$. In such alternative examples, the wearable device 100 can further include a circuit board 120 to mechanically support and electrically connect the various electronic components of the wearable device 100. The circuit board 120 can include an analog front end 122.

The wearable device 100 further includes a computing device 1200 for controlling the operation of the optical unit 110. The computing device 1200 includes at least one processing unit and a memory. In certain embodiments, the memory stores algorithms that when performed by the processing unit process the reflected and transmissive optical signals received by the light sensors 114 into $SpO_2$, PPG, and cuff-less blood pressure measurements of the subject S.

The wearable device 100 includes a transceiver 130 that transmits the calculated $SpO_2$, PPG, and cuff-less blood pressure measurements to the monitoring device 200 for display on the display device 204. Alternatively, the transceiver 130 can transmit raw, unprocessed data (i.e., the electrical signals 12) to the monitoring device 200, and the monitoring device 200 performs algorithms to calculate the $SpO_2$, PPG, and cuff-less blood pressure measurements of the subject S. In further alternative embodiments, the monitoring device 200 forwards the raw, unprocessed data (i.e., the electrical signals 12) to the server 1300, and the server 1300 performs algorithms to calculate the $SpO_2$, PPG, and cuff-less blood pressure measurements.

In certain embodiments, the wearable device 100 includes a power source 140 to power the various components of the wearable device 100 including the components of the optical unit 110 such as the light emitters 112 and light sensors 114. The power source 140 can include disposable or rechargeable batteries. In alternative embodiments, the wearable device 100 does not include a power source and instead receives electrical power from the monitoring device 200 such as through one or more electrical wires.

The wearable device 100 can be included in an assembly that includes additional sensors. For example, the wearable device 100 can be included in a patch worn by the subject S that includes additional sensors to noninvasively determine various vital signs such as body temperature, ECG, heart rate, breathing rate, cardiac output, stroke volume, and cuff-less blood pressure. In some embodiments, the wearable device 100 is included in a patch that calculate an early warning score based on the noninvasively determined vitals. The wearable device 100 whether included in a patch with additional sensors or used separately, can advantageously be worn in settings outside of a healthcare facility such as in the home of the subject S so that the vital signs of the subject S can be monitored remotely. The wearable device 100 can also be used for early deterioration detection such as before the subject S is admitted to a healthcare facility.

Figure 3:
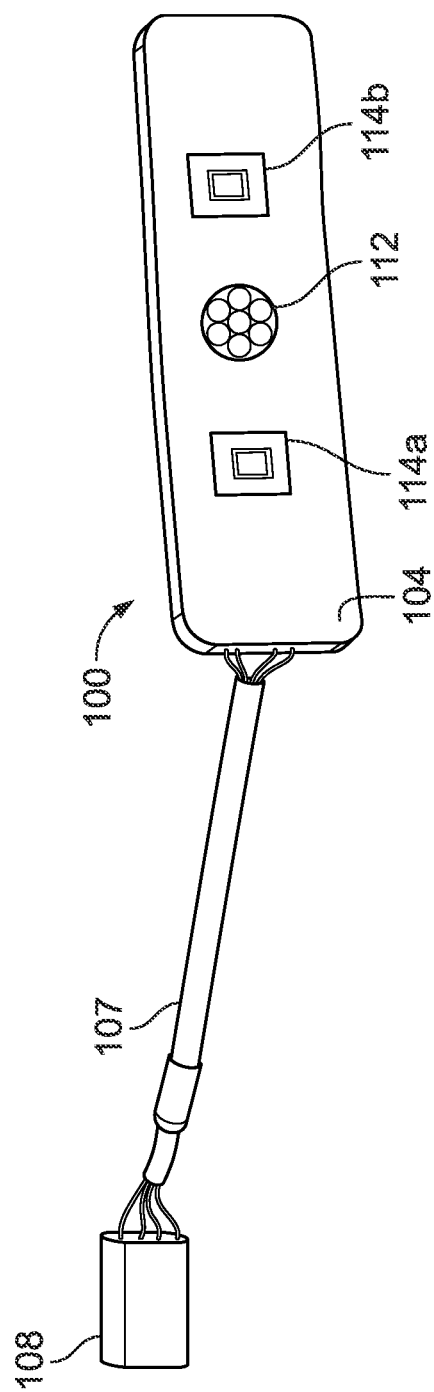
FIG. 3 is a bottom view of the wearable device.

FIG. 3 is a bottom view of the wearable device 100. As discussed above, the wearable device 100 includes one or more light emitters 112 that emit optical signals to illuminate blood vessels under a skin surface. The light emitters 112 are exposed through a bottom layer 104 such that the light emitted from the light emitters 112 has a direct path to the skin surface. The light emitters 112 emit optical signals in the form of infrared (IR) and visible red light.

In certain embodiments, the light emitters 112 include a plurality of LEDs that are arranged in a circular pattern. The arrangement of the plurality of LEDs in a circular pattern increases the surface area of the light emitters 112 which increases the amount of light that is directed to a skin surface and that can penetrate the skin surface where the wearable device 100 is attached. This is advantageous because in some instances it can be desirable to attach the wearable device 100 to the clavicle to measure $SpO_2$ and PPG, and this anatomical area has capillary beds that are less dense than other areas of the body. Thus, the arrangement of the plurality of LEDs can increase the penetration of light into capillary beds.

The plurality of LEDs may be controlled to sequence a transmission of visible red light and infrared light. In some embodiments, the visible red light has a wavelength of about 660 nm and the infrared light has a wavelength of about 940 nm. The plurality of LEDs sequences the transmission of the visible red light and infrared light by alternating back and forth between emitting the visible red light and the infrared light. As described above, absorption of infrared and visible red light differs significantly between oxygenated and deoxygenated blood.

The light sensors 114 are positioned on opposite sides of the light emitters 112. Thus, in some examples, the wearable device 100 includes two or more light sensors 114 (e.g., photodiodes) that are placed at a distance from the light emitters 112 (e.g., light-emitting diodes) to optimize the light collection through the tissue. For example, a first light sensor 114a is positioned on a first side of the light emitters 112 and a second light sensor 114b is positioned on an opposite, second side of the light emitters 112. In some examples, the first and second light sensors 114a, 114b are spaced by a distance of 10-20 mm from the light emitters 112. The position of the first and second light sensors 114a, 114b on opposite sides of the light emitters 112 increases the surface area of the light sensors 114a, 114b which increases the amount of reflective and transmissive optical signals absorbed by the light sensors 114a, 114b. This increases the signal-to-noise ratio of the optical signals, and improves the reliability and accuracy of the $SpO_2$ and PPG measurements calculated from the optical signals that are obtained by the wearable device 100 when the device is worn near the chest.

In the example illustrated in FIG. 3, the light emitters 112 and light sensors 114a, 114b are connected in parallel by wires 107 to a connector 108. The connector 108 can be plugged into the monitoring device 200 (see FIG. 4) to transmit the electrical signals 12 detected by the light sensors 114a, 114b of the wearable device 100 to the monitoring device 200. In alternative embodiments, the electrical signals 12 can be wirelessly transmitted to the monitoring device 200 without requiring use of the wires 107 or connector 108 such that the wearable device 100 is not physically connected to the monitoring device 200 by one or more wires.

Figure 4:
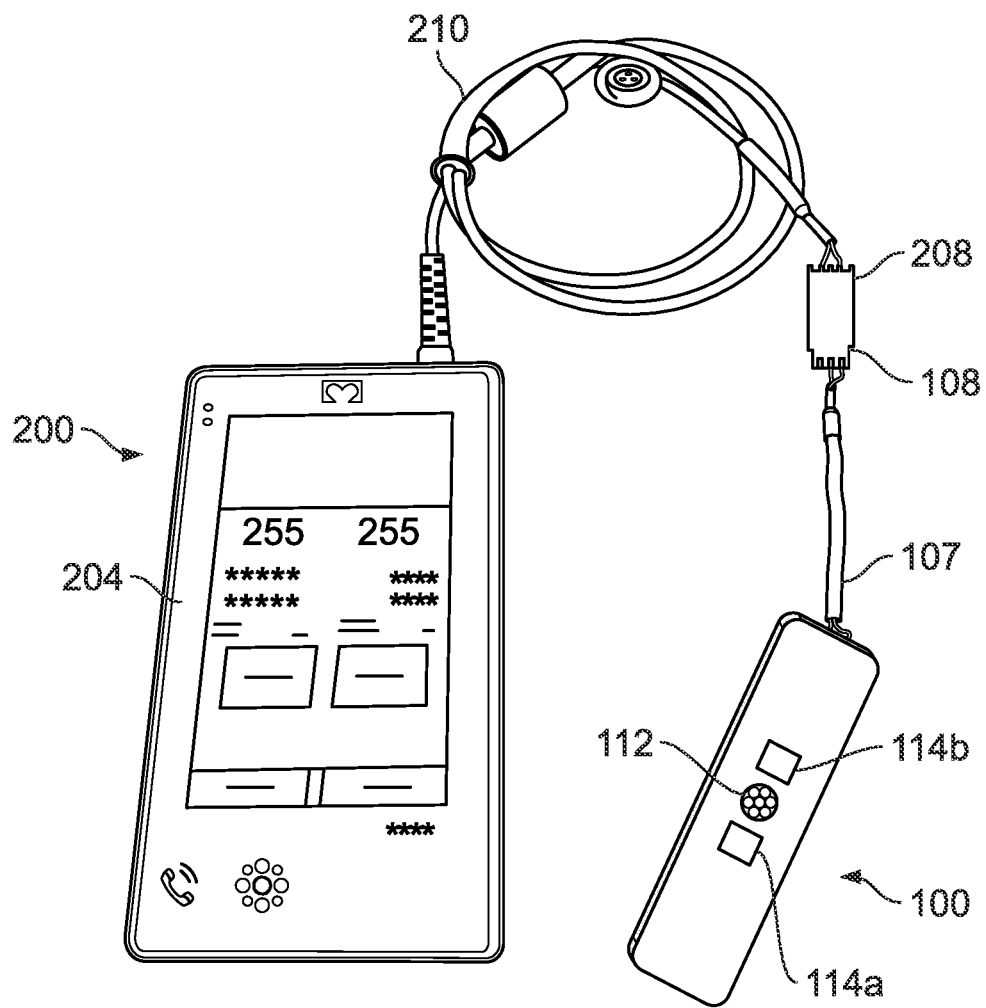
FIG. 4 is a view of the wearable device connected to a monitoring device.

FIG. 4 is a view of the wearable device 100 connected to the monitoring device 200. In the example embodiment illustrated in FIG. 4, the connector 108 of the wearable device 100 is connected into a corresponding connector 208 of the monitoring device 200 that terminates a distal end of a wire 210 that extends from the monitoring device 200. The monitoring device 200 includes the display device 204 to display one or more vital signs calculated from the electrical signals 12 such as $SpO_2$, PPG, and cuff-less blood pressure. The monitoring device 200 can provide electrical power to power the wearable device 100 through the wires 210, 107.

In alternative embodiments, the wearable device 100 wirelessly transmits the electrical signals 12 detected by the light sensors 114a, 114b to the monitoring device 200 such that the wearable device 100 does not include the wires 107 and connector 108. In such embodiments, the transceiver 130 of the wearable device 100 (see FIG. 2) and the analog front-end 202 of the monitoring device 200 (see FIG. 1) work together to provide a wireless connection between the wearable device 100 and the monitoring device 200 such as through Bluetooth, Wi-Fi, RFID, Near-Field Communication (NFC), ZigBee, and the like. Additionally, the wearable device 100 can have its own power source 140 (see FIG. 2) such as a disposable or rechargeable battery.

Figure 5:
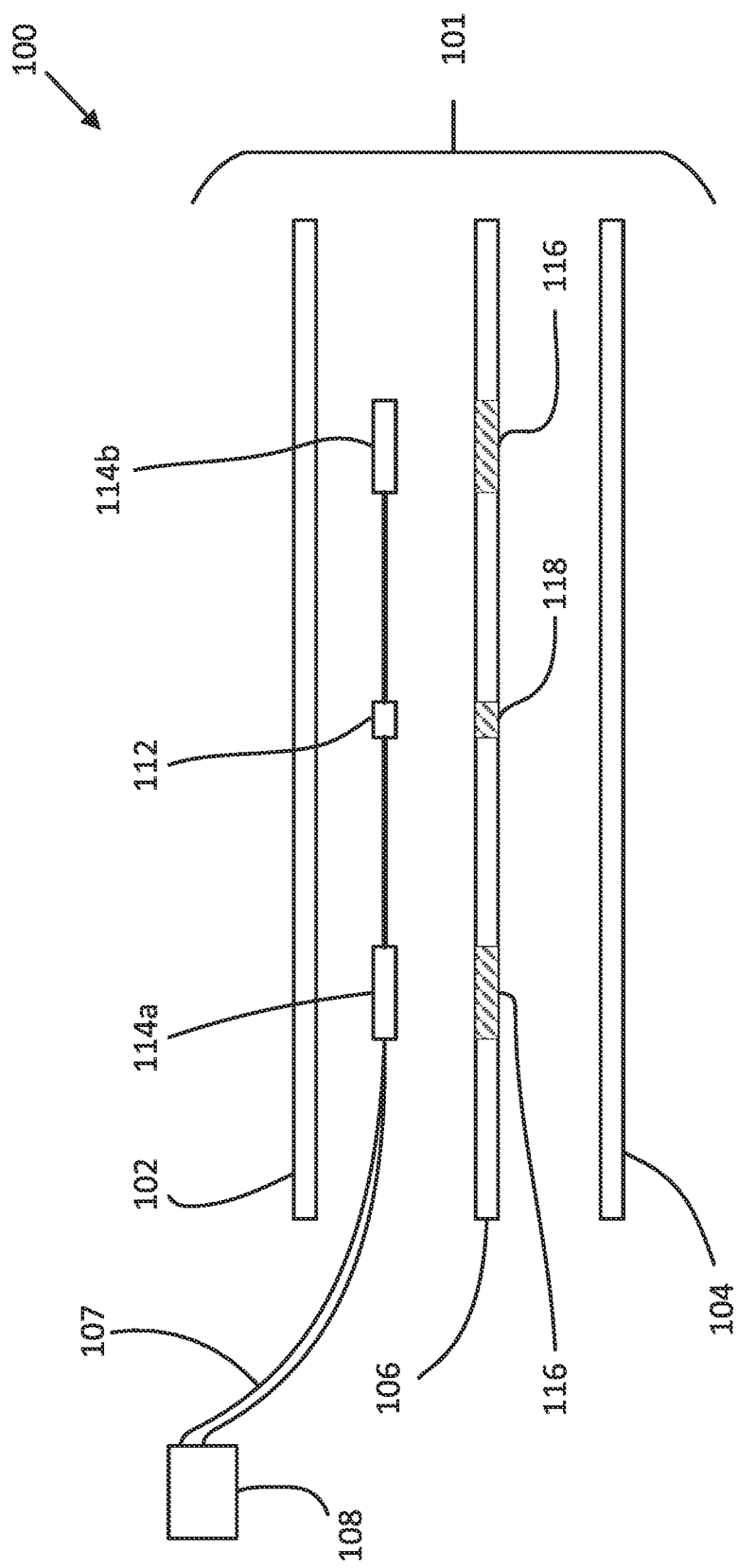
FIG. 5 is an exploded view of the wearable device.

FIG. 5 is an exploded view of the wearable device 100. Referring now to FIG. 5, the wearable device 100 includes a flexible housing 101 that is structured to flex around an anatomical structure near the chest of the subject S. The flexible housing 101 includes a foam layer 106 sandwiched between top and bottom layers 102, 104. The flexible housing 101 is structured to house the optical unit 110 (see FIG. 2) of the wearable device 100.

The flexible foam layer 106 includes cutouts 116 for housing the light sensors 114a, 114b and a cutout 118 for housing the light emitters 112. The flexible foam layer 106 can include additional cutouts to accommodate other components of the wearable device 100 such as the circuit board 120, transceiver 130, power source 140, and computing device 1200.

The top layer 102 protects the internal components of the wearable device 100 including the light emitters 112 and light sensors 114a, 114b from outside elements. The top layer 102 can include a flexible foam covered with a film to protect the wearable device 100 from water ingress and to prevent peeling of the wearable device 100 from the skin surface over the duration of wear. The film can also provide a waterproof, sterile barrier that protects the skin surface of the subject S from external contaminants such as liquids, bacteria, and viruses.

The bottom layer 104 provides a tight coupling of the wearable device 100 to a skin surface to maximize the light coupling from the light emitters 112 to the light sensors 114a, 114b. The bottom layer 104 can include a pressure-sensitive adhesive (PSA) that forms a bond between the wearable device 100 and a skin surface when pressure is applied to the wearable device 100 on the skin surface. The bond between the bottom layer 104 and the skin surface can last for five or more days so that the wearable device 100 can be continuously worn.

Figure 6:
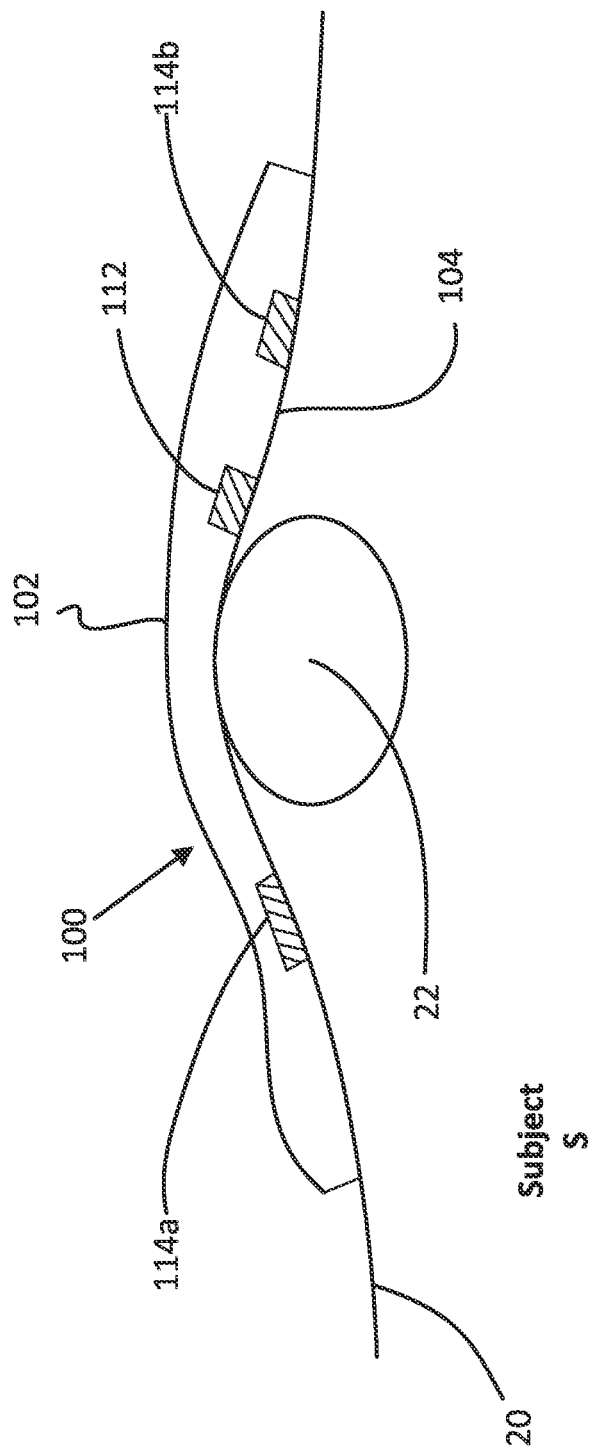
FIG. 6 is a cross-sectional view of the wearable device attached to a subject.

FIG. 6 is a cross-sectional view of the wearable device 100 attached to the subject S. In the example arrangement of FIG. 6, the bottom layer 104 is attached to a skin surface 20 next to the clavicle 22 of the subject S. FIG. 6 is provided as an illustrative example and is not drawn to scale. Thus, the positioning of the light emitters 112 to the light sensors 114a, 114b may vary depending on size of the subject and the clavicle bone, as well as the relative positioning of the wearable device 100 on the physical contour around the subject's clavicle. For example, in certain instances where the wearable device 100 is attached to the clavicle area, the light emitters 112 can be positioned directly on top of the clavicle instead of to the side as depicted in FIG. 6.

The flexibility of the wearable device 100 (including the flexible foam layer 106 sandwiched between the top and bottom layers 102, 104) allows the wearable device 100 to partially surround the clavicle 22. The flexibility of the wearable device 100 also allows the device to be attached to other skin surfaces and to thereby partially surround additional anatomical areas near the chest such as a shoulder blade or fold of skin in the axilla.

Advantageously, by partially surrounding an anatomical area near the chest of the subject S, the wearable device 100 can simultaneously receive both transmissive and reflective optical signals from arteriole beds near the chest. Thus, the wearable device 100 performs both transmission-mode pulse oximetry and reflection-mode pulse oximetry. This improves quality of the optical signals obtained from the wearable device 100 over other wearable devices that are only able to perform reflection-mode pulse oximetry near the chest of the subject.

Referring now to FIGS. 5 and 6, the wearable device 100 performs transmission-mode pulse oximetry by, for example, emitting the sequence of optical signals in the form of infrared (IR) and visible red light from the light emitters 112, and using the first and second light sensors 114a, 114b to collect the transmissive optical signals. In the illustrative example of FIG. 6, the light sensor 114a is located on an opposite side of the clavicle 22 from the light emitters 112 such that the light sensor 114a is positioned to collect transmissive optical signals. In alternative arrangements, the light sensor 114b can be located on an opposite side of the clavicle 22 from the light emitters 112 such that the light sensor 114b is positioned to collect transmissive optical signals. Thus, the positioning of the light sensors 114a, 114b on opposite sides of the light emitters 112 provides a technical effect by improving the ability to collect the transmissive optical signals that are transmitted through blood vessels around the clavicle 22.

Figure 7:
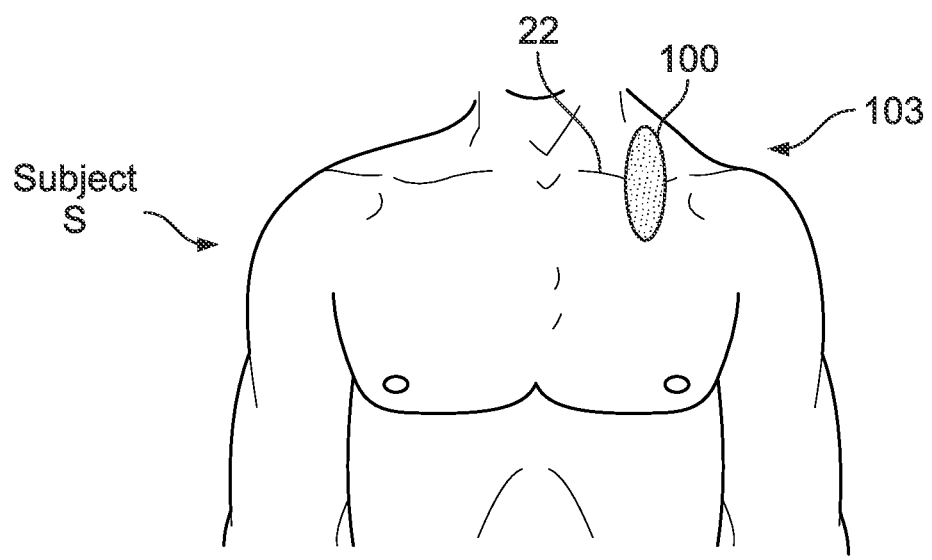
FIG. 7 is a view of a first placement orientation on a subject's chest.

FIG. 7 is a view of a first placement orientation 103 for the wearable device 100 when attached on the chest of the subject S. In the first placement orientation 103, the wearable device 100 is substantially orthogonal to the length of the clavicle 22. While FIG. 7 shows the wearable device 100 mounted over the left side clavicle, the first placement orientation 103 can also include mounting the wearable device 100 orthogonally over the right side clavicle.

Figure 8:
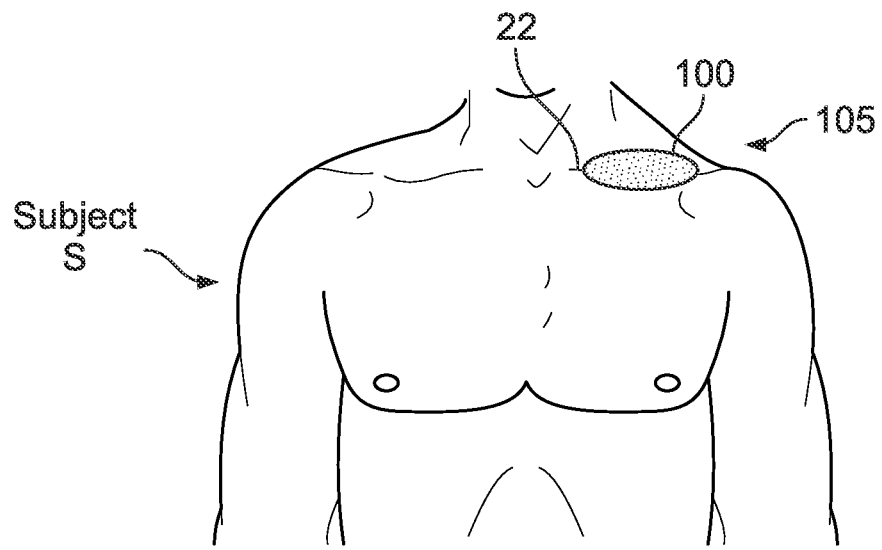
FIG. 8 is a view of a second placement orientation on the subject's chest.

FIG. 8 is a view of a second placement orientation 105 for the wearable device 100 when attached on the chest of the subject S. In the second placement orientation 105, the wearable device 100 is substantially parallel to the length of the clavicle 22. While FIG. 8 shows the wearable device 100 mounted over the left side clavicle, the second placement orientation 105 can also include mounting the wearable device 100 parallel over the right side clavicle. Also, in some instances, the wearable device 100 can be mounted below the clavicle 22 on the chest, in an orientation substantially parallel to the length of the clavicle 22. In such instances, the wearable device 100 is not mounted over the contours of the clavicle bone.

As described above, the flexibility of the wearable device 100 also allows the wearable device 100 to be attached to other skin surfaces and to thereby partially surround additional anatomical areas near the chest of the subject S such as in the axilla.

Figure 9:
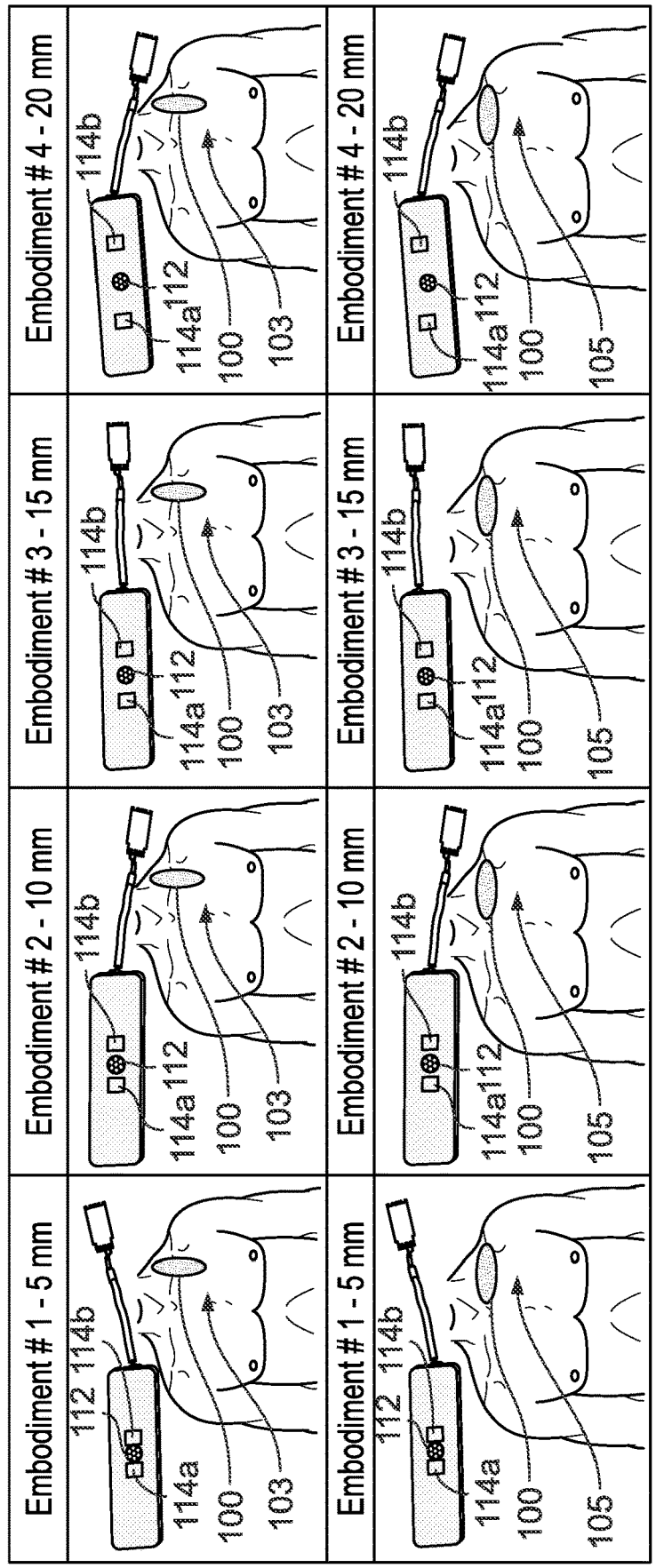
FIG. 9 is a table illustrating various placement orientations on the subject's chest.

FIG. 9 is a table 900 illustrating various placement orientations on the subject's chest. For example, in a first row of the table 900, the wearable device 100 is attached to the chest of the subject S in the first placement orientation 103 such that the wearable device 100 is substantially orthogonal to the length of the clavicle 22. In a second row of the table 900, the wearable device 100 is attached to the chest of the subject S in the second placement orientation 105 such that the wearable device 100 is substantially parallel to the length of the clavicle 22.

Also, the distance from the center of the light emitters 112 to the centers of the light sensors 114a, 114b that are respectively positioned on opposite sides of the light emitters 112 can be adjusted. For example, the centers of the light sensors 114a, 114b should be spaced far enough from the center of the light emitters 112 to ensure that the wavelengths of light emitted from the light emitters 112 travels through enough blood-perfused tissue. However, the centers of the light sensors 114a, 114b should be spaced close enough from the center of the light emitters 112 to ensure that the detected optical signals are primarily composed of the light energy emitted from the light emitters 112 and no other sources.

The centers of the light sensors 114 are spaced apart from the center of the light emitters 112 in a range of about 5 to 20 millimeters. For example, in a first column of the table 900, a first embodiment of the wearable device 100 has the centers of the light sensors 114 spaced apart from the center of the light emitters 112 by 5 millimeters. In a second column of the table 900, a second embodiment of the wearable device 100 has the centers of the light sensors 114 spaced apart from the center of the light emitters 112 by 10 millimeters. In a third column of the table 900, a third embodiment of the wearable device 100 has the centers of the light sensors 114 spaced apart from the center of the light emitters 112 by 15 millimeters. In a fourth column of the table 900, a first embodiment of the wearable device 100 has the centers of the light sensors 114 spaced apart from the center of the light emitters 112 by 20 millimeters.

The placement orientations (e.g., the first placement orientation 103 vs. the second placement orientation 105) and the distance from the center of the light emitters 112 to the centers of the light sensors 114a, 114b (e.g., columns 1-4 of table 900) can be adjusted to optimize the performance of the wearable sensor 100 to obtain reliable and accurate $SpO_2$ and PPG measurements. Additional orientations and embodiments are contemplated.

Figure 10:
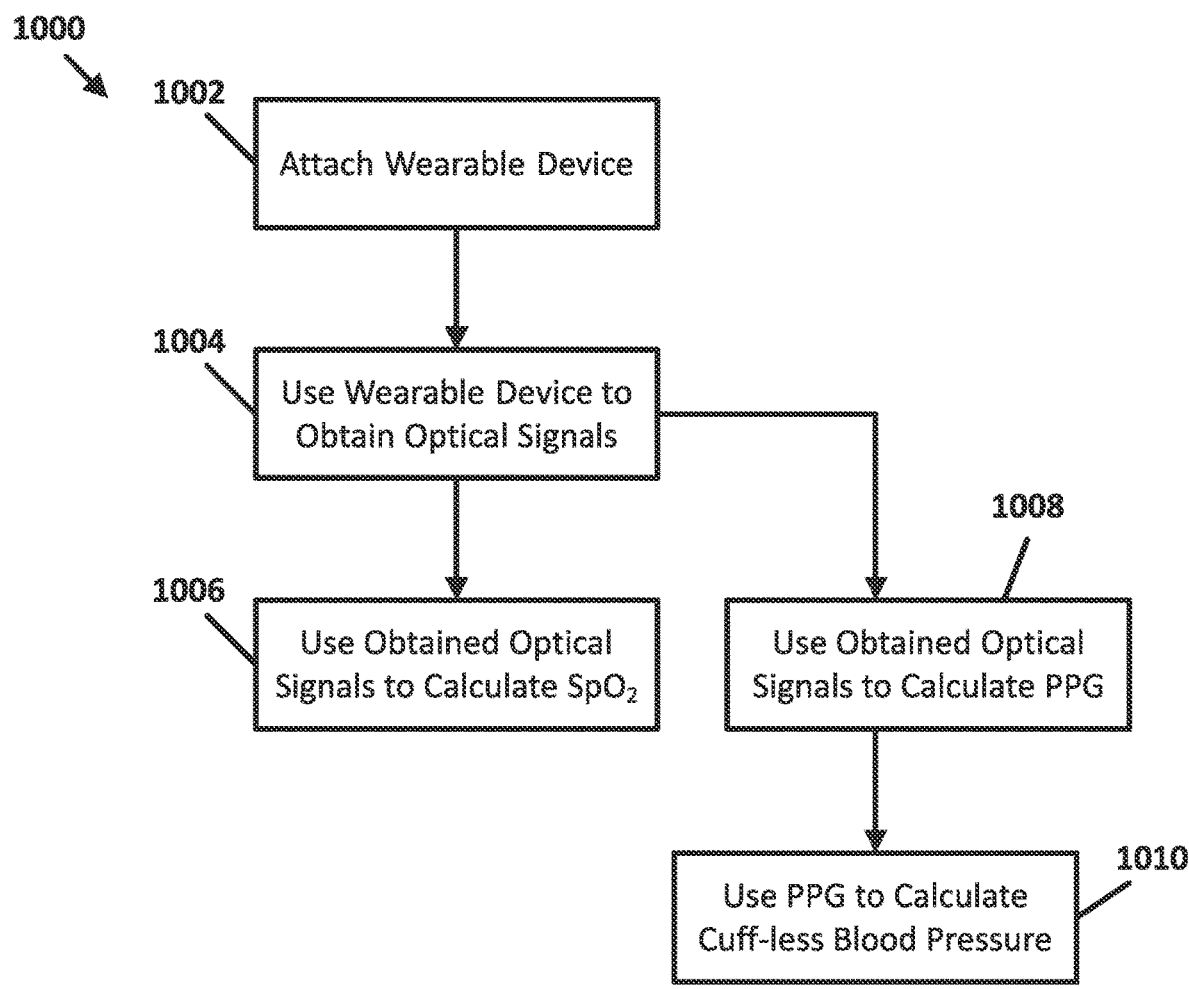
FIG. 10 schematically illustrates a method of measuring peripheral oxygen saturation near the chest of a subject.

FIG. 10 schematically illustrates a method 1000 of measuring peripheral oxygen saturation ($SpO_2$) near the chest of the subject S. The method 1000 includes an operation 1002 of attaching the wearable device 100 to the subject S such that the device partially surrounds an anatomical area near the chest of the subject S.

In some embodiments, the anatomical area is the clavicle, and operation 1002 includes placing the wearable device 100 substantially orthogonal to the length of the clavicle (i.e., the first placement orientation 103) or placing the wearable device 100 substantially parallel to the length of the clavicle (i.e., second placement orientation 105). In some embodiments, the anatomical area is a fold of skin in the axilla, and operation 1002 includes placing the wearable device 100 to partially surround the fold of skin in the axilla. In some further embodiments, the anatomical area is a shoulder blade, and operation 1002 includes placing the wearable device 100 to partially surround the shoulder blade.

Next, the method 1000 includes an operation 1004 of using the wearable device 100 to obtain optical signals from the anatomical area near the chest of the subject S. In one embodiment, the optical signals include both reflective and transmissive optical signals. In alternative embodiments, optical signals include only reflective optical signals. In further alternative embodiments, optical signals include only transmissive optical signals.

Next, the method 1000 includes an operation 1006 of using the obtained optical electrical signals to calculate the $SpO_2$ measurement of the subject S. In some embodiments, the wearable device 100 remains attached to the subject S for an extended period of time such that the $SpO_2$ measurement of the subject S is continuously updated and monitored. In some embodiments, the wearable device 100 is worn continuously by the subject S for five or more days to continuously monitor and update the $SpO_2$ for five or more days.

The method 1000 can include a further operation 1008 of using the obtained optical signals to calculate a PPG measurement of the subject S. In some embodiments, the method includes both operations 1006 and 1008. In some embodiments, the method 1000 does not include operation 1008 such that operation 1008 is optional. In some further embodiments, operation 1008 replaces operation 1006 such that the method 1000 calculates a PPG measurement of the subject S instead of the $SpO_2$ measurement.

In some embodiments, the method 1000 can include a further operation 1010 of using the PPG measurement to calculate a cuff-less blood pressure of the subject S. In embodiments where the wearable device 100 remains attached to the subject S for an extended period of time, the cuff-less blood pressure of the subject S can be continuously updated and monitored.

Figure 11:
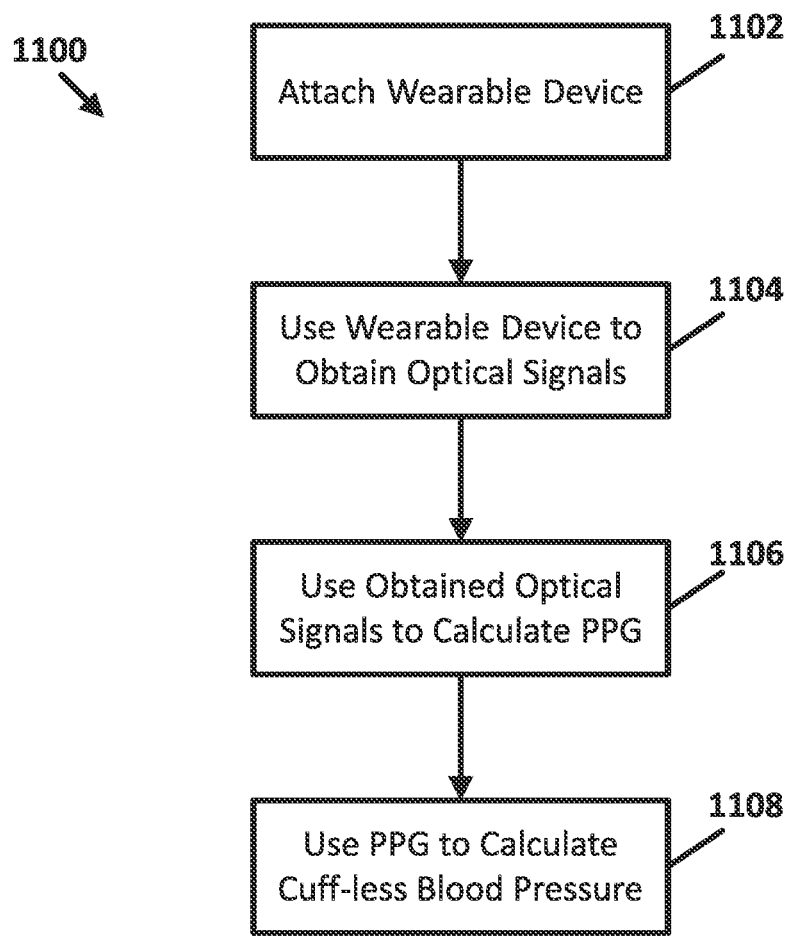
FIG. 11 schematically illustrates a method of measuring cuff-less blood pressure.

FIG. 11 schematically illustrates a method 1100 of measuring cuff-less blood pressure. The method 1100 includes operation 1102 of attaching the wearable device 100 to the subject S such that the device partially surrounds an anatomical area near the chest.

In some embodiments, the anatomical area is the clavicle, and operation 1102 includes placing the wearable device 100 substantially orthogonal to the clavicle (i.e., the first placement orientation 103) or placing the wearable device 100 substantially parallel to the clavicle (i.e., the second placement orientation 105). In some embodiments, the anatomical area is a fold of skin in the axilla, and operation 1102 includes placing the wearable device 100 to partially surround the fold of skin in the axilla. In further embodiments, the anatomical area is a shoulder blade, and operation 1002 includes placing the wearable device 100 to partially surround the shoulder blade.

Next, the method 1100 includes an operation 1104 of using the wearable device 100 to obtain optical signals from the anatomical area near the chest of the subject S. In a preferred embodiment, the optical signals include both reflective and transmissive optical signals. In alternative embodiments, optical signals include only reflective optical signals. In further alternative embodiments, optical signals include only transmissive optical signals.

Next, the method 1100 includes an operation 1106 of using the obtained optical signals to calculate PPG measurement of the subject S. In some embodiments, the wearable device 100 remains attached to the subject S for an extended period of time such that the PPG measurement of the subject S is continuously updated and monitored. In some embodiments, the wearable device 100 is worn continuously by the subject S for five or more days to continuously monitor and update the PPG for five or more days.

Next, the method 1100 includes an operation of 1108 of using the PPG measurement to calculate a cuff-less blood pressure of the subject S. In embodiments where the wearable device 100 remains attached to the subject S for an extended period of time, the cuff-less blood pressure of the subject S can be continuously updated and monitored.

Figure 12:
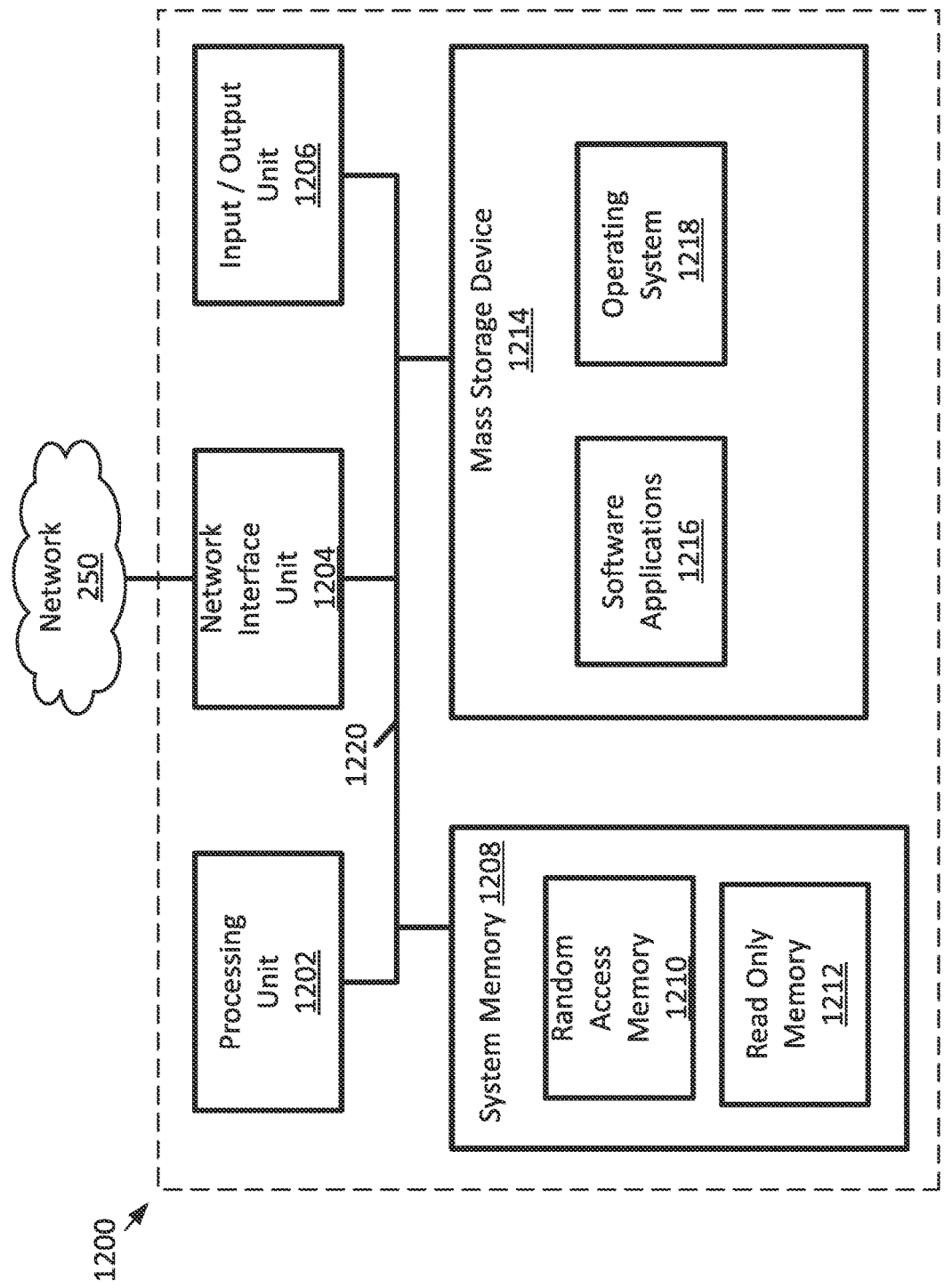
FIG. 12 illustrates an exemplary architecture of a computing device that can be used to implement aspects of the present disclosure.

FIG. 12 illustrates an exemplary architecture of a computing device 1200 which can be used to implement aspects of the present disclosure, such as the functions of the wearable device 100 and monitoring device 200 described above. The computing device 1200 includes a processing unit 1202, a system memory 1208, and a system bus 1220 that couples the system memory 1208 to the processing unit 1202. The processing unit 1202 is an example of a processing device such as a central processing unit (CPU). The system memory 1208 includes a random-access memory ("RAM") 1210 and a read-only memory ("ROM") 1212. A basic input/output logic containing the basic routines that help to transfer information between elements within the computing device 1200, such as during startup, is stored in the ROM 1212.

The computing device 1200 can also include a mass storage device 1214 that is able to store software instructions and data. The mass storage device 1214 is connected to the processing unit 1202 through a mass storage controller (not shown) connected to the system bus 1220. The mass storage device 1214 and its associated computer-readable data storage media provide non-volatile, non-transitory storage for the computing device 1200.

Although the description of computer-readable data storage media contained herein refers to a mass storage device, it should be appreciated by those skilled in the art that computer-readable data storage media can be any available non-transitory, physical device or article of manufacture from which the device can read data and/or instructions. The mass storage device 1214 is an example of a computer-readable storage device.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, or any other medium which can be used to store information, and which can be accessed by the device.

The computing device 1200 may operate in a networked environment using logical connections to remote network devices through the network 250, such as a local network, the Internet, or another type of network. The device connects to the network 250 through a network interface unit 1204 connected to the system bus 1220. The network interface unit 1204 may also be utilized to connect to other types of networks and remote computing systems.

The computing device 1200 can also include an input/output controller 1206 for receiving and processing input from a number of input devices. Similarly, the input/output controller 1206 may provide output to a number of output devices.

The mass storage device 1214 and the RAM 1210 can store software instructions and data. The software instructions can include an operating system 1218 suitable for controlling the operation of the device. The mass storage device 1214 and/or the RAM 1210 also store software instructions 1216, that when executed by the processing unit 1202, cause the device to provide the functionality of the device discussed in this document. For example, the mass storage device 1214 and/or the RAM 1210 can store software instructions that, when executed by the processing unit 1202, cause the wearable device to send or receive vital signs measurements.

The various embodiments described above are provided by way of illustration only and should not be construed to be limiting in any way. Various modifications can be made to the embodiments described above without departing from the true spirit and scope of the disclosure.

What is claimed is:

1. A wearable device for sensing vital signs comprising:
    a flexible housing;
    at least one light emitter attached to the flexible housing, the at least one light emitter configured to emit optical signals; and
    light sensors attached to the flexible housing, the light sensors being positioned on opposite sides of the at least one light emitter, wherein the light sensors include a first light sensor positioned on a first side of the at least one light emitter and a second light sensor positioned on a second side of the least one light emitter, wherein the second side is opposite the first side, and wherein the first and second light sensors are equally spaced apart from the at least one light emitter;
    wherein the flexible housing is structured to attach to a skin surface and flex at least partially around an anatomical structure enabling the light sensors to receive both reflective and transmissive optical signals near a chest of a subject.

2. The wearable device of claim 1, wherein the optical signals include infrared and visible red light wavelengths.

3. The wearable device of claim 1, wherein the at least one light emitter includes a plurality of light-emitting diodes.

4. The wearable device of claim 3, wherein the plurality of light-emitting diodes includes at least one light-emitting diode configured to emit visible light and at least one light-emitting diode configured to emit infra-red light.

5. The wearable device of claim 3, wherein the plurality of light-emitting diodes are arranged in a circular pattern.

6. The wearable device of claim 1, wherein the light sensors are spaced apart from the at least one light emitter in a range between 5 and 20 millimeters.

7. The wearable device of claim 1, wherein the flexible housing includes a foam layer sandwiched between top and bottom layers, and wherein the foam layer includes cutouts for housing the light sensors and the at least one light emitter.

8. The wearable device of claim 7, wherein the top layer includes a flexible foam covered with a film to protect the light sensors and the at least one light emitter from water ingress and to prevent peeling of the wearable device from the skin surface.

9. The wearable device of claim 7, wherein the bottom layer includes a pressure-sensitive adhesive that forms a bond between the wearable device and the skin surface when pressure is applied to the wearable device on the skin surface.

10. The wearable device of claim 1, wherein the anatomical structure is a clavicle bone, a fold of skin in an axilla, or a shoulder blade.

11. A method of measuring peripheral oxygen saturation, the method comprising:
    attaching a wearable device around an anatomical structure near a chest such that the wearable device partially surrounds the anatomical structure near the chest;
    using the wearable device to obtain optical signals near the chest, wherein the obtained optical signals include reflective optical signals reflected back from blood vessels and transmissive optical signals transmitted through the blood vessels; and
    using the obtained optical signals to calculate peripheral oxygen saturation.

12. The method of claim 11, wherein the anatomical structure is a clavicle bone, a fold of skin in an axilla, or a shoulder blade.

13. The method of claim 12, wherein attaching the wearable device around the anatomical structure includes attaching the wearable device orthogonally with respect to the clavicle bone.

14. The method of claim 11, further comprising:
    using the obtained optical signals to calculate a photoplethysmogram.

15. The method of claim 14, further comprising:
    using the photoplethysmogram to calculate cuff-less blood pressure.

16. A wearable device for sensing vital signs comprising:
    a flexible housing;
    an optical unit positioned inside the flexible housing, the optical unit including:
        light emitters that emit a transmission sequence of optical signals;
        light sensors positioned on opposite sides of the light emitters, wherein the light sensors include a first light sensor positioned on a first side of the light emitters and a second light sensor positioned on a second side of the light emitters, wherein the second side is opposite the first side, and wherein the first and second light sensors are equally spaced apart from the light emitters; and
    wherein the flexible housing is structured to attach to a skin surface and flex around an anatomical structure enabling the light sensors to receive both reflective and transmissive optical signals near a chest of a subject.

17. The wearable device of claim 16, wherein the light emitters are multi-wavelength light emitters that emit light in a plurality of wavelength spectrums, and the light sensors collect multi-spectral measurements of tissue and fluid near the chest.

18. The wearable device of claim 16, wherein the anatomical structure is a clavicle bone, a fold of skin in an axilla, or a shoulder blade.

* * * * *